US011667616B2

United States Patent
Ji et al.

(10) Patent No.: US 11,667,616 B2
(45) Date of Patent: Jun. 6, 2023

(54) ORAL GSNOR INHIBITOR AND PHARMACEUTICAL USE THEREOF

(71) Applicant: NANJING MEDICAL UNIVERSITY, Jiangsu (CN)

(72) Inventors: Yong Ji, Jiangsu (CN); Liping Xie, Jiangsu (CN); Shuang Zhao, Jiangsu (CN); Tianyu Song, Jiangsu (CN); Yi Han, Jiangsu (CN)

(73) Assignee: NANJING MEDICAL UNIVERSITY, Jiangsu (CN)

( * ) Notice: Subject to any disclaimer, the term of this patent is extended or adjusted under 35 U.S.C. 154(b) by 0 days.

(21) Appl. No.: 17/628,904

(22) PCT Filed: Apr. 25, 2021

(86) PCT No.: PCT/CN2021/089594
§ 371 (c)(1),
(2) Date: Jan. 21, 2022

(87) PCT Pub. No.: WO2022/141977
PCT Pub. Date: Jul. 7, 2022

(65) Prior Publication Data
US 2022/0372007 A1 Nov. 24, 2022

(30) Foreign Application Priority Data
Dec. 31, 2020 (CN) .......................... 202011622515.7

(51) Int. Cl.
*C07D 277/02* (2006.01)
*A61P 11/06* (2006.01)
*C07D 417/14* (2006.01)

(52) U.S. Cl.
CPC ............ *C07D 277/02* (2013.01); *A61P 11/06* (2018.01); *C07D 417/14* (2013.01)

(58) Field of Classification Search
None
See application file for complete search history.

(56) References Cited

U.S. PATENT DOCUMENTS

2015/0005352 A1  1/2015  Cohen et al.

FOREIGN PATENT DOCUMENTS

| CN | 102186478 | 9/2011 |
|---|---|---|
| CN | 109943622 | 6/2019 |
| CN | 109999029 | 7/2019 |
| CN | 111529524 | 8/2020 |
| WO | 2010019903 | 2/2010 |
| WO | 2010019905 | 2/2010 |
| WO | 2010019910 | 2/2010 |

OTHER PUBLICATIONS

"International Search Report (Form PCT/ISA/210) of PCT/CN2021/089594," dated Sep. 28, 2021, pp. 1-6.
"Written Opinion of the International Searching Authority (Form PCT/ISA/237) of PCT/CN2021/089594" dated Sep. 28, 2021, with English translation thereof, pp. 1-7.

*Primary Examiner* — Jeffrey S Lundgren
*Assistant Examiner* — Michael J Schmitt
(74) *Attorney, Agent, or Firm* — JCIPRNET

(57) ABSTRACT

Disclosed are a thiazolone derivative of N6022 and a pharmaceutical use thereof. The characteristic structure of the thiazolone derivative of N6022 is:

Compared to N6022, the compound of the present disclosure has good oral bioavailability and a longer half-life period. In in-vitro experiments, administering the compound of the present disclosure can improve migration ability, tube formation ability and, the permeability of human umbilical vein endothelial cells caused by high glucose, and administering the compound of the present disclosure at an animal level can obviously promote the angiogenesis and blood flow recovery of ischemic lateral limbs of diabetic mice. Overall, it suggests that the compound of the present disclosure can be used for treating diseases related to diabetic vascular complications.

2 Claims, 8 Drawing Sheets

ORAL GSNOR INHIBITOR AND PHARMACEUTICAL USE THEREOF

CROSS-REFERENCE TO RELATED APPLICATION

This application is a 371 of international application of PCT application serial no. PCT/CN2021/089594, filed on Apr. 25, 2021, which claims the priority benefit of China application no. 202011622515.7, filed on Dec. 31, 2020. The entirety of each of the above mentioned patent applications is hereby incorporated by reference herein and made a part of this specification.

BACKGROUND

Technical Field

The present invention relates to a thiazolone derivative of an s-nitrosoglutathione reductase (GSNOR) N6022 and a pharmaceutical use thereof, and in particular to a use thereof for preparing medicines for improvement and treatment on diseases related to asthma, cystic fibrosis, diabetic vascular complications and aortic aneurysm/dissection.

Description of Related Art

N6022 is a specific and reversible s-nitrosoglutathione reductase (GSNOR) inhibitor; and studies have shown that N6022 can effectively mitigate asthma and allergic airway inflammation. The phase I and phase II clinical trials of N6022 for treating chronic asthma and cystic fibrosis have finished.

Diabetes has become a leading health problem causing morbidity and mortality worldwide. 70% of the deaths of the diabetic patients are attributed to cardiovascular complications; and the diabetic vascular complications, including atherosclerosis, peripheral arterial diseases, retinopathy and nephropathy, are also major factors affect the quality of life. Vascular endothelial cells are located on the inner membrane of the vascular wall and serve as a barrier between blood and tissues. Under various physiological and pathological conditions, the endothelial cells can also play a role as "first response" effector cells for adjusting vascular functions. Diabetes induces endothelial cell dysfunction which is mainly manifested by an increase in vascular endothelial permeability, an impairment of angiogenesis ability. This impairment constitutes a main inducement and a pathophysiological basis of various vascular complications. Although the molecular mechanism of the diabetic endothelial dysfunction has been widely studied, there are limited numbers of method for treating diabetic vascular complications. Therefore, it is key to seek for a new clinically effective method to treat diabetic vascular complications and reduce the disability rate and mortality rate.

Aortic aneurysm/dissection (AAD), a highly fatal disease without effective treatment drug, is one of the common diseases threatening human health. Aortic intima is locally torn due to some pathological factors, resulting in gradual peeling and expansion under the impact of blood flow, so that a true cavity and a false cavity are formed in the artery. The rupture of the aortic dissection will cause serious consequences such as hemorrhagic shock and cardiac tamponade, and even sudden death. AAD often attacks people aged between 65 and 75, and its main risk factors include hypertension, dyslipidemia and heritable connective tissue diseases like Marfan syndrome. The mortality rate of AAD is 50-68% within 48 hours after onset and increased to 90% within 3 months. Therefore, AAD has the characteristics of a fast progress, complex conditions with high fatality rate. The key to clinically effectively reducing the high fatality rate is to seek a new effective method for treating AAD.

We have found that N6022 shows beneficial effect on both the diabetic vascular complications and the aortic aneurysm/dissection, but the clinical use of N6022 is limited due to its low oral bioavailability and fast metabolism.

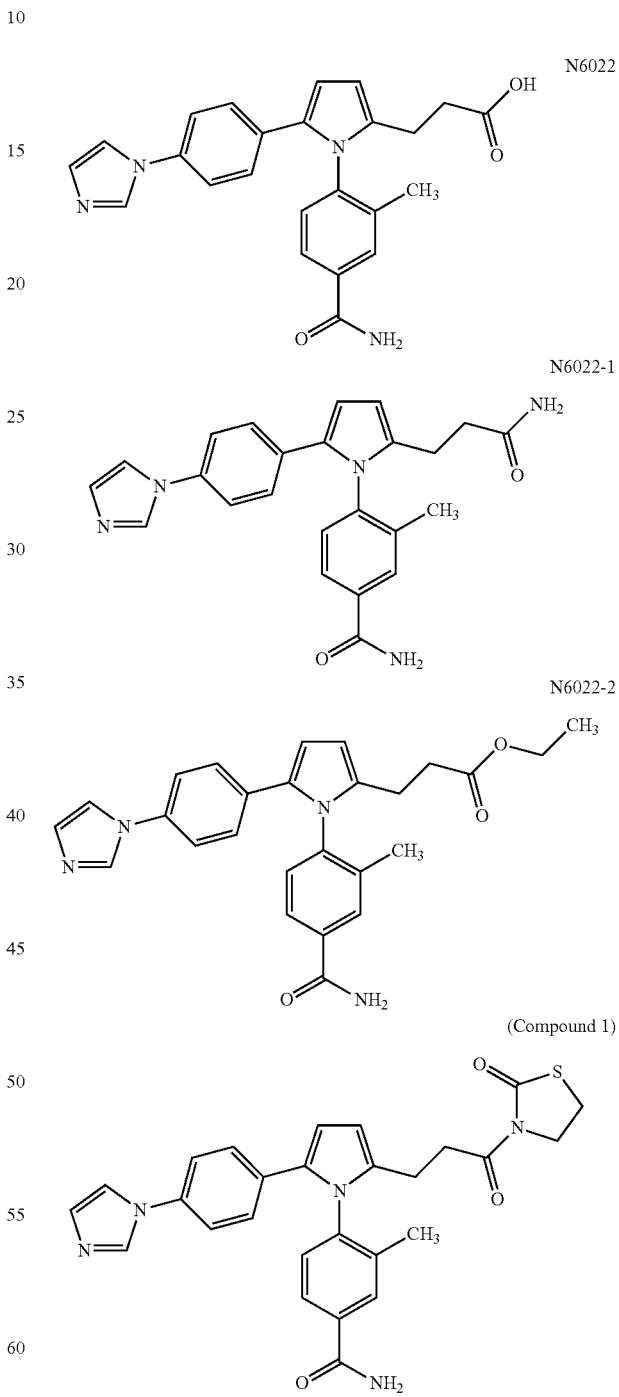

The applicant has conducted a structural modification of N6022 and found that the activities of an amide derivative N6022-1 and an ester derivative N6022-2 of N6022 are significantly reduced in in-vitro studies. Quite surprisingly, we have found that a thiazolone derivative (subject compound 1) of N6022 shows a good activity in vitro and has good bioavailability, and that at the same dose, the subject compound 1 has a significantly better oral efficacy than N6022, N6022-1 and N6022-2.

SUMMARY

Technical problem to be solved: The present disclosure provides a thiazolone derivative of N6022, which has preeminent in-vitro and in-vivo activities and bioavailability, a longer half-life period, and can be used for preparing medicine for improvement and treatment on diseases related to asthma, cystic fibrosis, diabetic vascular complications and aortic aneurysm/dissection.

Technical solution: A thiazolone derivative of N6022 having the following characteristic structure:

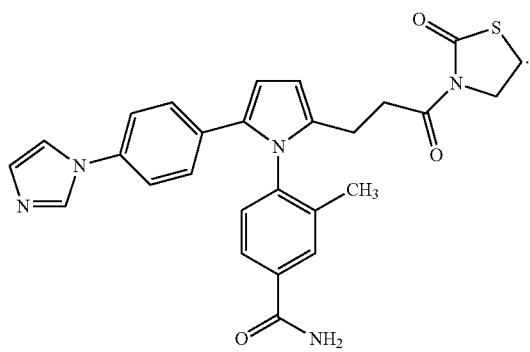 [SMILES: Cc1cc(C(N)=O)ccc1-n1c(CCC(=O)N2CCSC2=O)ccc1-c1ccc(-n2ccnc2)cc1]

The subject compound 1 has good in-vitro and in-vivo activities and bioavailability, and a longer half-life period, and can be used for preparing medicines for improvement and treatment on diseases related to asthma, cystic fibrosis, diabetic vascular complications and aortic aneurysm/dissection.

Beneficial effects: The subject compound 1 has good in-vitro and in-vivo activities and bioavailability, and a longer half-life period, and can be used for preparing medicines for improvement and treatment on diseases related to asthma, cystic fibrosis, diabetic vascular complications and aortic aneurysm/dissection.

DESCRIPTION OF THE EMBODIMENTS

The examples below are used to further describe the content of the present disclosure, but should not be interpreted as a limitation. All modifications and substitutions made to the methods, steps or conditions of the present disclosure are within the protection scope of the present disclosure. Unless otherwise specified, the technical means used in the examples are conventional means to those skilled in the art.

Example 1

Synthesis of s4-(2-(4-(1H-imidazol-1-yl)phenyl)-5-(3-oxo-3-(2-oxothiazolidin-3-yl)propyl)-1H-pyrrol-1-yl)-3-methylbenzamide (Subject Compound 1)

Figure 1:
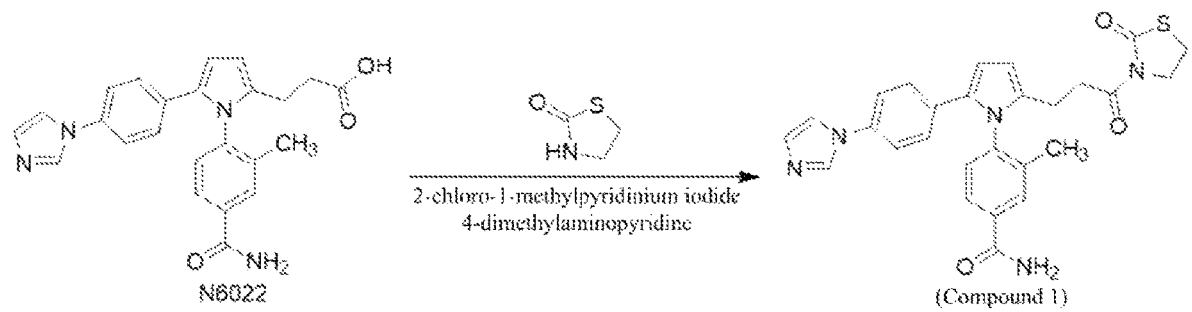
FIG. 1: Synthesis route of the subject compound 1.

FIG. 1 shows the synthesis route:

Synthesis Route:

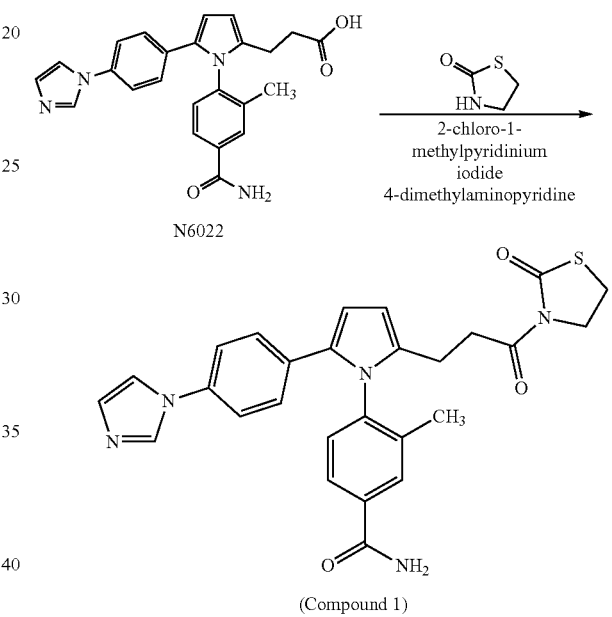

(Compound 1)

Experimental Procedure:

3-(5-(4-(1H-imidazol-1-yl)phenyl)-1-(4-carbamoyl-2-methylphenyl)-1H-pyrrol-2-yl) propanoic acid (N6022, 500 mg, 1.21 mmol), 2-chloro-1-methylpyridinium iodide (CMPI, 370 mg, 1.45 mmol), dimethylaminopyridine (DMAP, 10 mg, 0.06 mmol), thiazolidone (250 mg, 2.41 mmol) and triethylamine (TEA, 490.2 mg, 4.84 mmol) were sequentially added into a 250 ml single-neck flask, and dichloromethane (15 ml) was added; and the reaction occurred at room temperature for 8 hours. Suction filtration was performed; the pH of the filtrate was adjusted to 7 using dilute hydrochloric acid; dichloromethane (15 ml) and water (15 ml) were added for extraction; organic phases were combined and subjected to rotary evaporation to dry; column chromatography separation (dichloromethane:methanol=25:1) was performed to obtain 400 mg of a beige crude product; and the beige crude product was recrystallized from absolute methanol to obtain 195 mg of a white solid, with a yield of 32%.

$^1$H NMR (Chloroform-d, 400 MHz) δ (ppm): δ 7.81-7.67 (m, 3H), 7.39 (d, J=7.6 Hz, 1H), 7.30-7.10 (m, 2H), 6.84 (s, 1H), 6.40 (s, 1H), 6.13 (s, 1H), 4.06 (s, 2H), 3.22 (s, 2H), 3.02 (s, 2H), 2.60 (s, 2H), 1.82 (s, 3H).

Example 2

Study of the In Vitro Activity of the Subject Compound 1 Against Asthma and Cystic Fibrosis (Taking N6022, N6022-1 and N6022-2 as Controls)

GSNOR plays a crucial regulatory role in asthma and cystic fibrosis. The GSNOR activity in the lungs of asthma patients is significantly increased, and allelic mutations of GSNOR significantly increase the probability of asthma in children. Also, the GSNOR activity in the respiratory tracks of cystic fibrosis patients is obviously increased, whereas the level of its catalytic product GSNO is decreased significantly. In order to explore the protective effect of the subject compound 1 in asthma and cystic fibrosis, the inhibitory effects of the subject compound 1, N6022, N6022-1 and N6022-2 on the GSNOR activity were tested in vitro.

Figure 2:
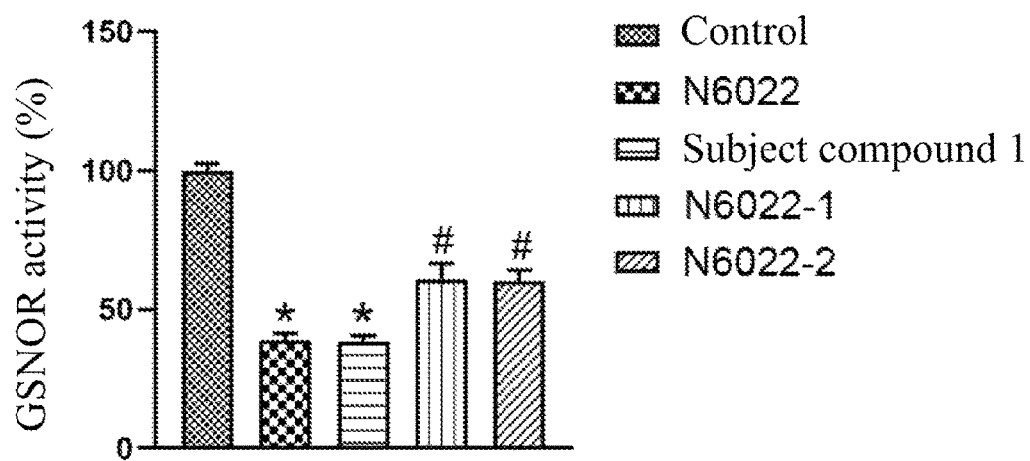
FIG. 2: Study of the in vitro activity of the subject compound 1 against asthma and cystic fibrosis.

FIG. 2 shows study of the in vitro activity of the subject compound 1 against asthma and cystic fibrosis. Human umbilical vein endothelial cells (HUVECs) were treated with N6022, the subject compound 1, N6022-1 and N6022-2 (10 nM) for 24 hours treatment, respectively; then, the cell lysate supernatants were treated with a substrate GSNO and a coenzyme NADH for 5 minutes reaction; the consumption of NADH per minute was detected through a characteristic absorption peak of NADH at 340 nm; and the activity of GSNOR was calculated; *$P<0.05$ vs Control, #$P<0.05$ vs Subject compound 1, n=3.

The results show that the subject compound 1 is equivalent to N6022 in the inhibitory effect on the GSNOR activity, and is significantly superior to N6022-1 and N6022-2. This suggests that the subject compound 1 showed equivalent in-vitro activity to N6022 in the against asthma and cystic fibrosis.

Example 3

Study of the In-Vitro Activity of the Subject Compound 1 Against Diabetic Vascular Complications (Taking N6022, N6022-1 and N6022-2 as Controls)

It is known that in the diabetic vascular complications, decreased angiogenesis and increased vascular endothelial permeability are among the risk factors causing local edema, ischemia followed by ulcer and amputation. In order to study the therapeutic effect of the subject compound 1 on the diabetic vascular complications at cellular level, HUVECs were challenged with a high glucose (30 mM) stimulus, as well as the subject compound 1, N6022, N6022-1 and N6022-2 (10 nM) respectively for 24 hours to test the angiogenesis ability of the endothelial cells through an endothelial cell tube formation experiment.

Figure 3A:
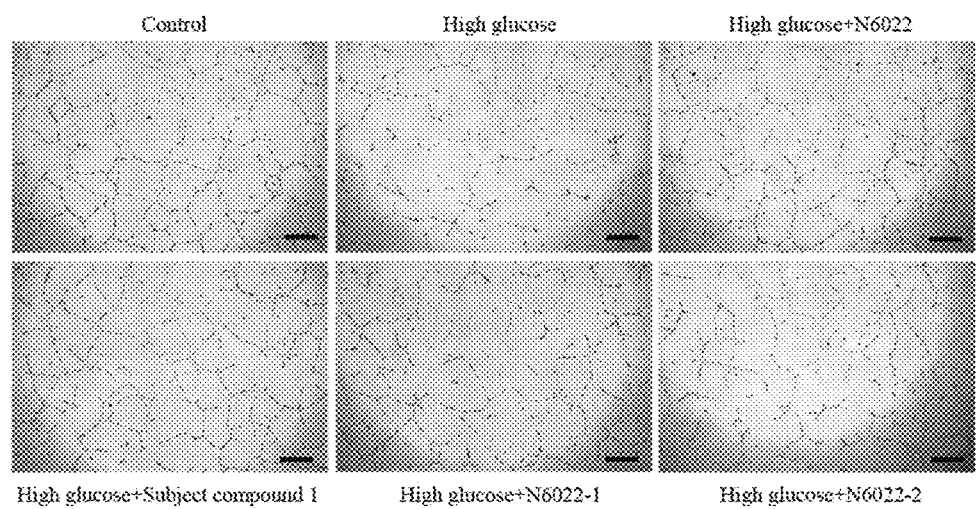
FIG. 3A, FIG. 3B and FIG. 3C: Study of the in vitro activity of the subject compound 1 against diabetic vascular complications.
Figure 3A:
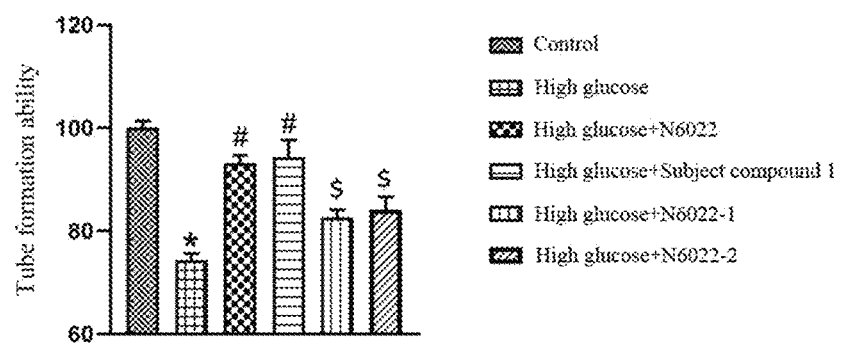
Figure 3B:
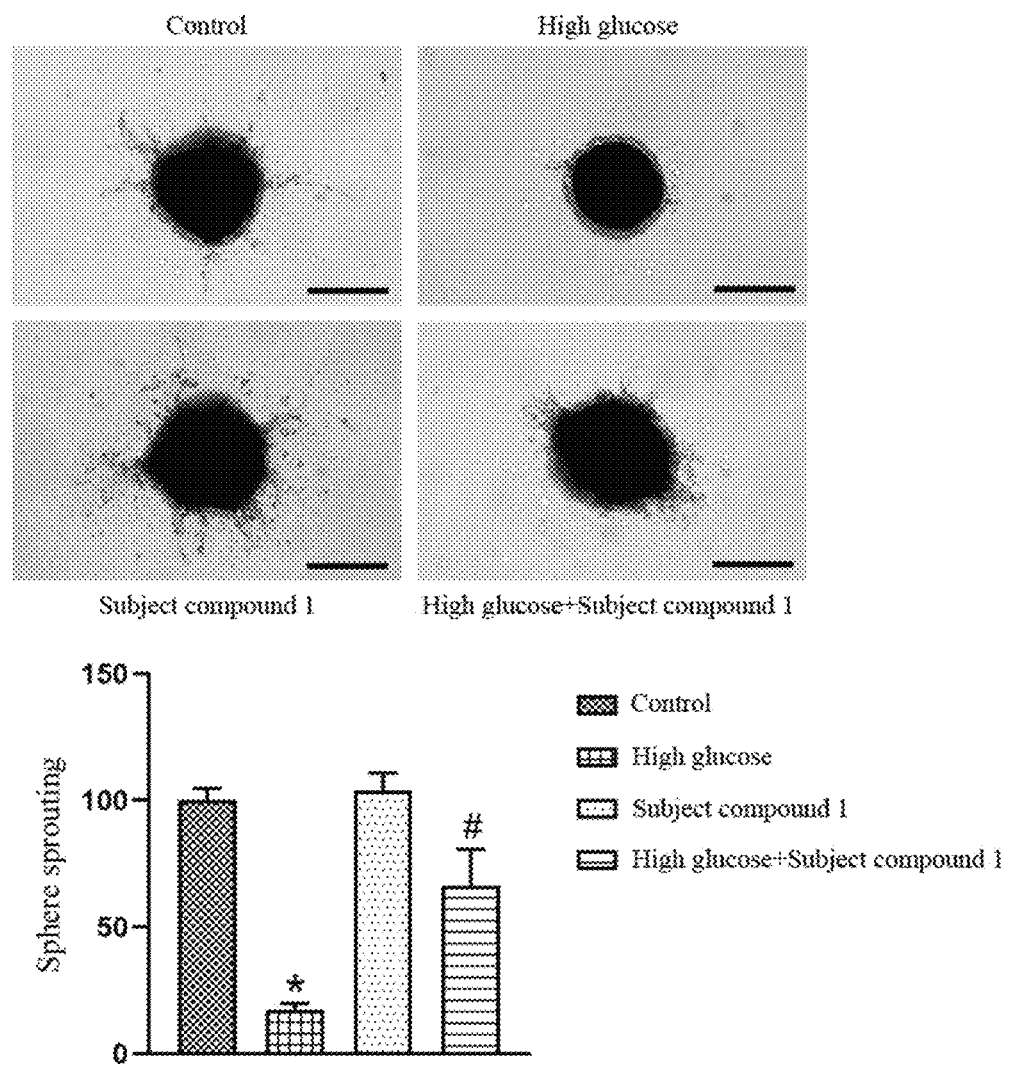
Figure 3C:
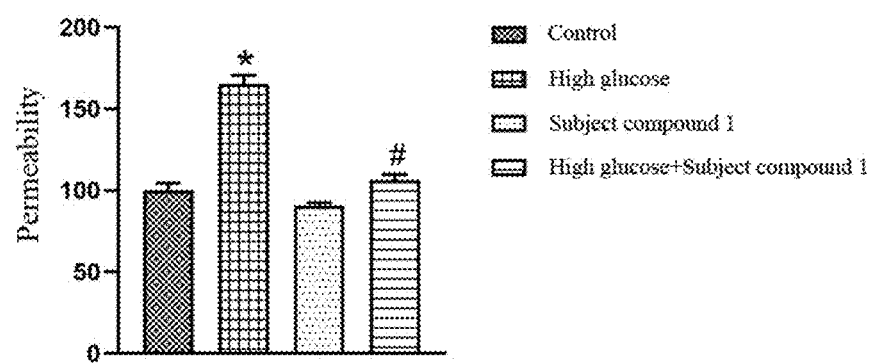

FIG. 3A, FIG. 3B and FIG. 3C show study of the in-vitro activity of the subject compound 1 against diabetic vascular complications. HUVECs were pretreated with high glucose (30 mM), then divided into following three groups: A) HUVECs were given with N6022, the subject compound 1, N6022-1 and N6022-2 (10 nM) for 24 h treatment, respectively, and the tube formation ability of the endothelial cells was measured; scale=200 μm, *$P<0.05$ vs Control, #$P<0.05$ vs High glucose, $$P<0.05$ vs High glucose+subject compound 1, n=3; B) the HUVECs were given with the subject compound 1 (10 nM) for 24 h treatment, and the sprouting ability of the endothelial cells was measured; scale=200 μm, *$P<0.05$ vs Control, #$P<0.05$ vs High glucose, n=3; and C) HUVECs were given with the subject compound 1 (10 nM) for 24 h treatment, and the permeability of the endothelial cells was measured; *$P<0.05$ vs Control, #$P<0.05$ vs High glucose, n=3.

The results show that the subject compound 1 and N6022 can obviously improve the high glucose caused defects in angiogenesis ability of endothelial cells, and showed a significantly better outcome than N6022-1 and N6022-2 (FIG. 3A); and the results of the sphere sprouting experiment and the permeability experiment show that the subject compound 1 can improve sprouting ability and modify the permeability of the endothelial cells due to high glucose (FIG. 3B-FIG. 3C), suggesting that the subject compound 1 has a good therapeutic effect on the diabetic vascular complications.

Example 4

Study of the In-Vitro Activity of the Subject Compound 1 Against Aortic Aneurysm/Dissection Diseases (Taking N6022, N6022-1 and N6022-2 as Controls)

In order to explore the protective effect of the subject compound 1 in the aortic aneurysm/dissection, at a cellular level, we have given human aortic smooth muscle cells (HASMCs) with angiotensin II (1 μM), as well as the subject compound 1, N6022, N6022-1 and N6022-2 (10 nM) respectively for 24 hours treatment. Then, cellular RNA were extracted to detect contractile/synthetic markers of smooth muscle cells.

Figure 4:
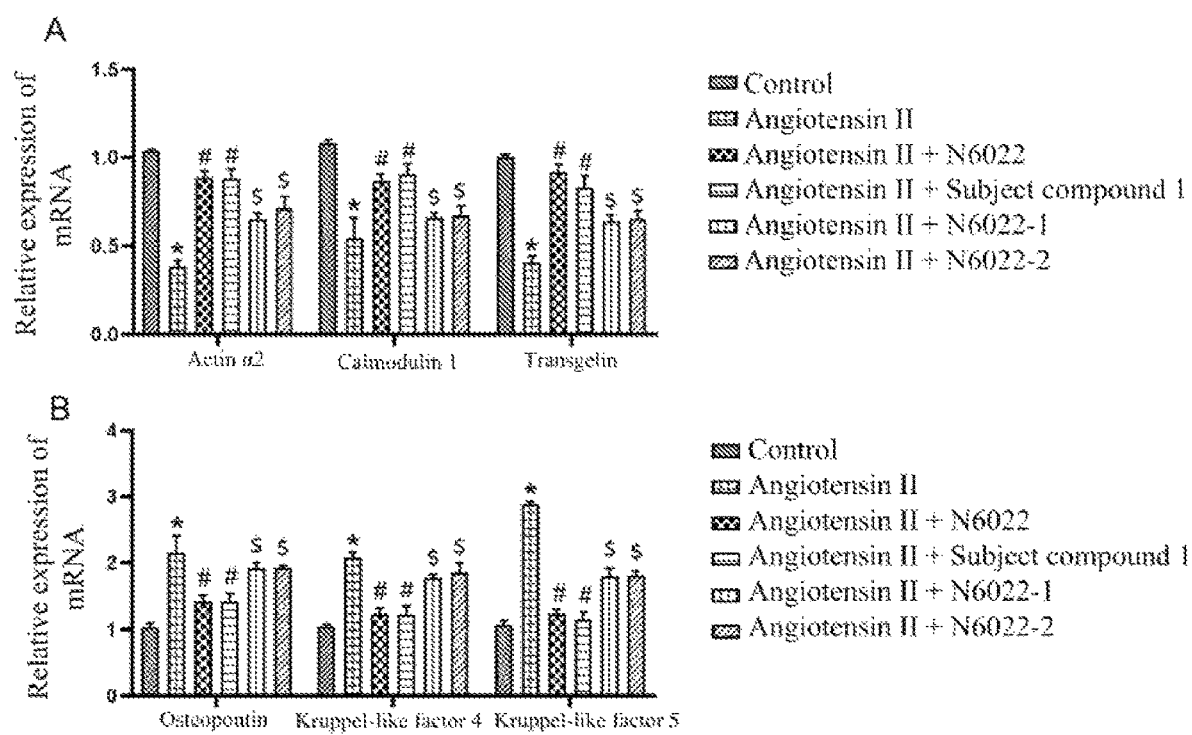
FIG. 4: Study of the in vitro activity of the subject compound 1 against aneurysm/dissection diseases.

FIG. 4 shows study of the in-vitro activity of the subject compound 1 against aneurysm/dissection diseases. HASMCs were given with angiotensin II (1 μM), as well as N6022, the subject compound 1, N6022-1 and N6022-2 (10 nM) respectively for 24 hours treatment; and the cellular RNA was extracted, where A: the expression of contractile markers (actin α2, calmodulin 1 and transgelin) of smooth muscle cells was detected; and B: the expression of synthetic markers (osteopontin, Kruppel-like factor 4 and Kruppel-like factor 5) of smooth muscle cells was detected; *$P<0.05$ vs Control, #$P<0.05$ vs Angiotensin II, $$P<0.05$ vs Angiotensin II+Subject compound 1, n=3.

The results show that the subject compound 1 and N6022 can obviously inhibit a decrease in the expression of the contractile markers and an increase in the expression in the synthetic markers due to angiotensin II, so as to inhibit phenotypic switch of the smooth muscle cells, and has a significantly better effect than N6022-1 and N6022-2 (FIG. 4A-B). This suggests that compared to N6022-1 and N6022-2, the subject compound 1 presents a better therapeutic effect on the aortic aneurysm/dissection diseases.

Example 5

Study of the Oral Bioavailability of the Subject Compound 1 (Taking N6022 as a Control)

In order to verify the oral bioavailability of the subject compound 1, ICR mice were treated with single intravenous injection dose of N6022 (1 mg/kg) and the subject compound 1 (1.2 mg/kg) respectively. Two other groups were treated with N6022 (5 mg/kg) and the subject compound 1 (6 mg/kg) respectively at a single oral dose. Then, the plasma concentration was detected by LC-MS/MS at hour 0.083, 0.25, 0.5, 1, 2, 4, 8 and 24 respectively (FIG. 5).

Figure 5:
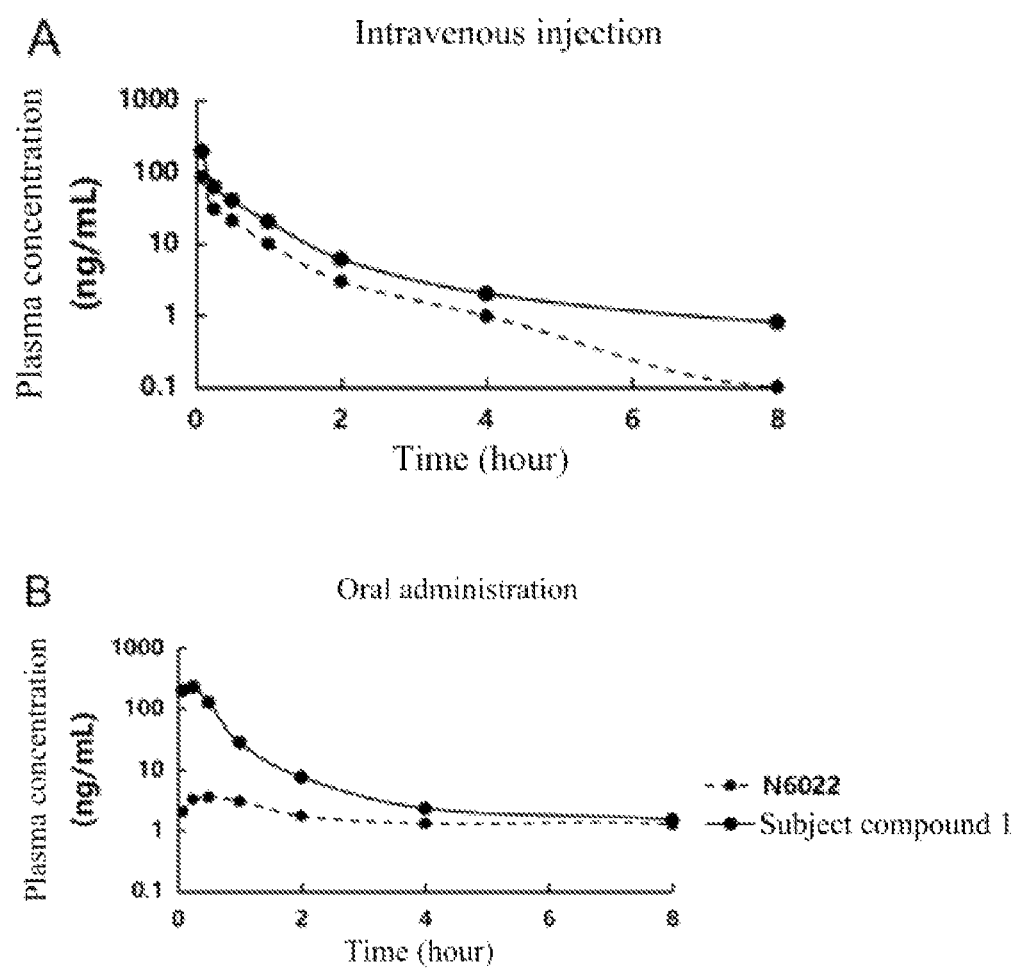
FIG. 5: Pharmacokinetic study of the subject compound 1 vs N6022.

FIG. 5 shows pharmacokinetic study of the subject compound 1 vs N6022. A: ICR mice were given with N6022 (1 mg/kg) and the subject compound 1 (1.2 mg/kg) at a single intravenous injection dose; and B: ICR mice were given with N6022 (5 mg/kg) and the subject compound 1 (6 mg/kg) at a single oral dose; and the plasma concentration was detected through LC-MS/MS at hour 0.083, 0.25, 0.5, 1, 2, 4, 8 and 24; n=3.

The results show that compared to N6022, the oral bioavailability of the subject compound 1 is obviously increased (60.07±7.91% vs 6.44±3.72%), and the drug half-life period is also prolonged (1.62±0.81 vs 0.76±0.15 h); and the experiments above indicate that the subject compound 1 has good oral bioavailability.

Example 6

Study of the Oral Efficacy of the Subject Compound 1 on Diabetic Vascular Complications (Taking N6022, N6022-1 and N6022-2 as Controls)

In order to further study the oral efficacy of the subject compound 1 on diabetic vascular complications, SPF-level 8-week-old male C57BL/6J mice (purchased from the Medical Experimental Animal Center of Nanjing Medical University) were randomly divided into six groups: a control group, a diabetes model group, a diabetes model+gavage with subject compound 1 (6 mg/kg/day) group, a diabetes model+gavage with N6022-1 (5.6 mg/kg/day) group, a diabetes model+gavage with N6022-2 (5.3 mg/kg/day) group, and a diabetes model+intravenous injection with N6022 (1 mg/kg/day) group. To generate diabetes model, mice at week 8 were intraperitoneally injected with streptozotocin (60 mg/kg/day) for consecutive 5 days, then the modeling was identified as a success if the blood glucose was measured to be greater than 16.6 mmol/L at week 10. For the mice of all groups, a lateral limb ischemia model was established at week 12; and after operation, the groups were given with N6022, the subject compound 1, N6022-1 and N6022-2 every day, and the blood flow recoveries of the lateral limbs were monitored with a laser speckle blood flow imaging system at day 0, 7 and 14 respectively (FIG. 6A). The gastrocnemius muscles of the ischemic lateral limbs of the mice were isolated for frozen section, and immunofluorescence (platelet-endothelial cell adhesion molecule, CD31) was used to detect the angiogenesis (FIG. 6B); and the semimembranosus muscles were isolated for frozen section, and immunofluorescence (α-smooth muscle actin, α-SMA) was used to detect the arteriogenesis (FIG. 6B).

Figure 6:
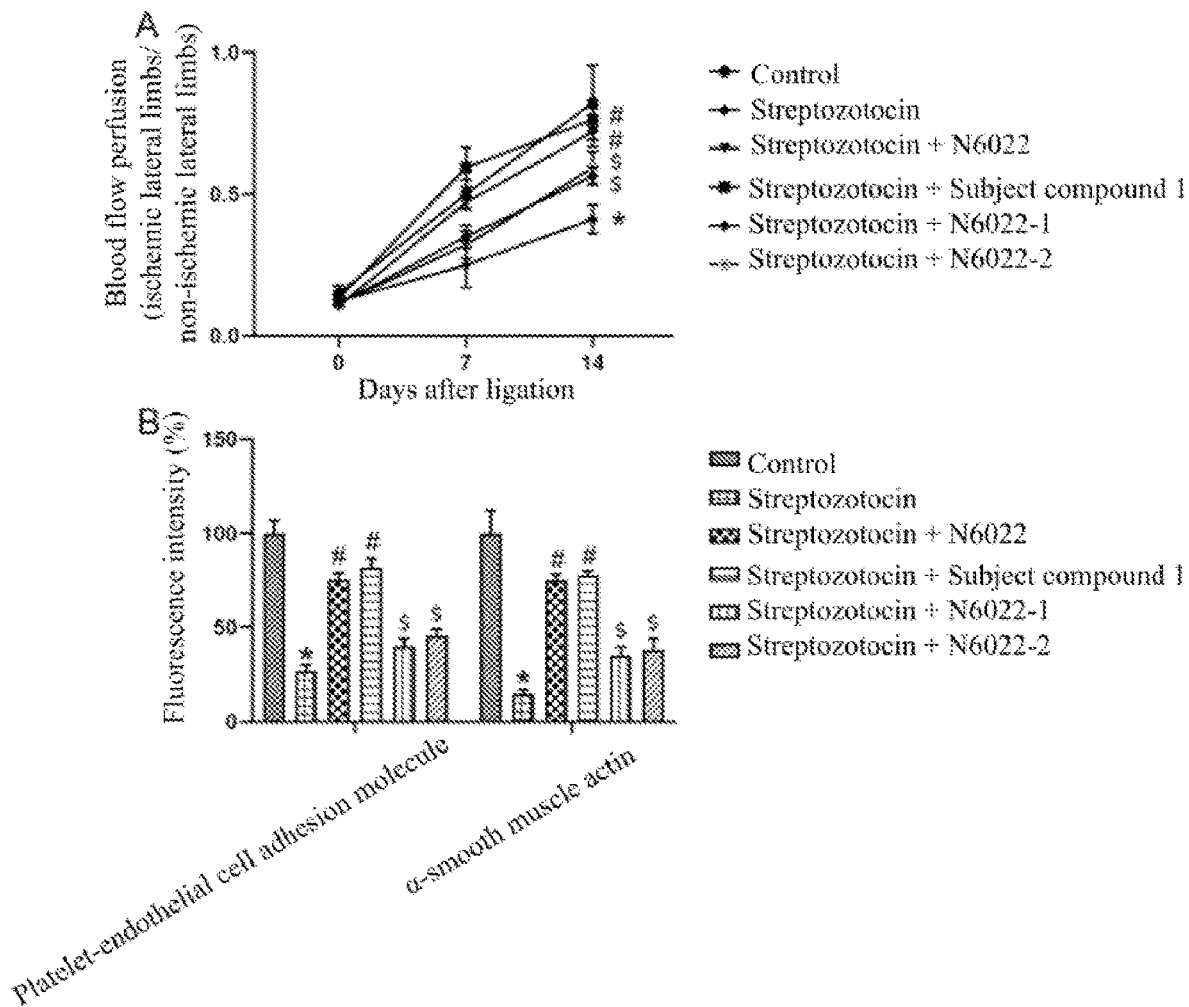
FIG. 6: Study of the oral efficacy of the subject compound 1 on diabetic vascular complications.

FIG. 6 shows study of the oral efficacy of the subject compound 1 on diabetic vascular complications. 8-week-old male C57BL/6J mice were intraperitoneally injected with streptozotocin (60 mg/kg/day) for consecutive 5 days, and if the blood glucose was measured to be greater than 16.6 mmol/L at week 10, then the diabetes modeling was identified as a success; then, a lateral limb ischemia model was established for the mice at week 12, and after operation, the mice were intravenously injected with N6022 (1 mg/kg/day), gavaged with the subject compound 1 (6 mg/kg/day), gavaged with N6022-1 (5.6 mg/kg/day) and gavaged with N6022-2 (5.3 mg/kg/day) every day, where A: the blood flow recoveries of the lateral limbs were monitored with a laser speckle blood flow imaging system at day 0, 7 and 14; and B: the gastrocnemius muscles and semimembranosus muscles of the ischemic left limbs of the mice were removed for frozen section, and immunofluorescent staining was performed using a platelet-endothelial cell adhesion molecule (CD31) antibody and an α-smooth muscle actin (α-SMA) antibody respectively, and the neogenesis of the capillaries and arteries was detected; *P<0.05 vs Control, #P<0.05 vs Streptozotocin, $P<0.05 vs Streptozotocin+Subject compound 1, n=3.

The results show that oral administration of the subject compound 1 can obviously promote the angiogenesis of the ischemic lateral limbs of the diabetic mice, thus to restore blood flow, which has an equivalent effect to the group intravenously injected with N6022 and a significantly better effect than the groups orally administered with N6022-1 and with N6022-2; and the experiments above indicate that oral administration of the subject compound 1 showed desirable therapeutic effect on diabetic vascular complications.

Example 7

Study of the Oral Efficacy of the Subject Compound 1 on Aortic Aneurysm/Dissection Diseases (Taking N6022, N6022-1 and N6022-2 as Controls)

In order to further study the oral efficacy of the subject compound 1 on aortic aneurysm/dissection diseases, SPF-level 3-week-old male C57BL/6J mice (purchased from the Medical Experimental Animal Center of Nanjing Medical University) were randomly divided into six groups: a control group, a disease model group (0.25% β-aminopropionitrile-containing drinking water, 28 days), a disease model+gavage with subject compound 1 (6 mg/kg/day) group, a disease model+gavage with N6022-1 (5.6 mg/kg/day) group, a disease model+gavage with N6022-2 (5.3 mg/kg/day) group, and a disease model+intravenous injection with N6022 (1 mg/kg/day) group. The results show that the mice of the disease model group using β-aminopropionitrile-containing drinking water alone experience obvious pathologic expansion in the aortas, where the diameters of the ascending aorta/descending aorta/thoracic aorta are about 1.5 times higher than control group, and the mortality rate and the incidence rate of aortic dissection are significantly increased compared to the control group; and after the mice of the disease model group are gavaged with the subject compound 1, both the expansion of the aortic diameter and the mortality rate of the mice are inhibited (FIG. 7).

Figure 7:
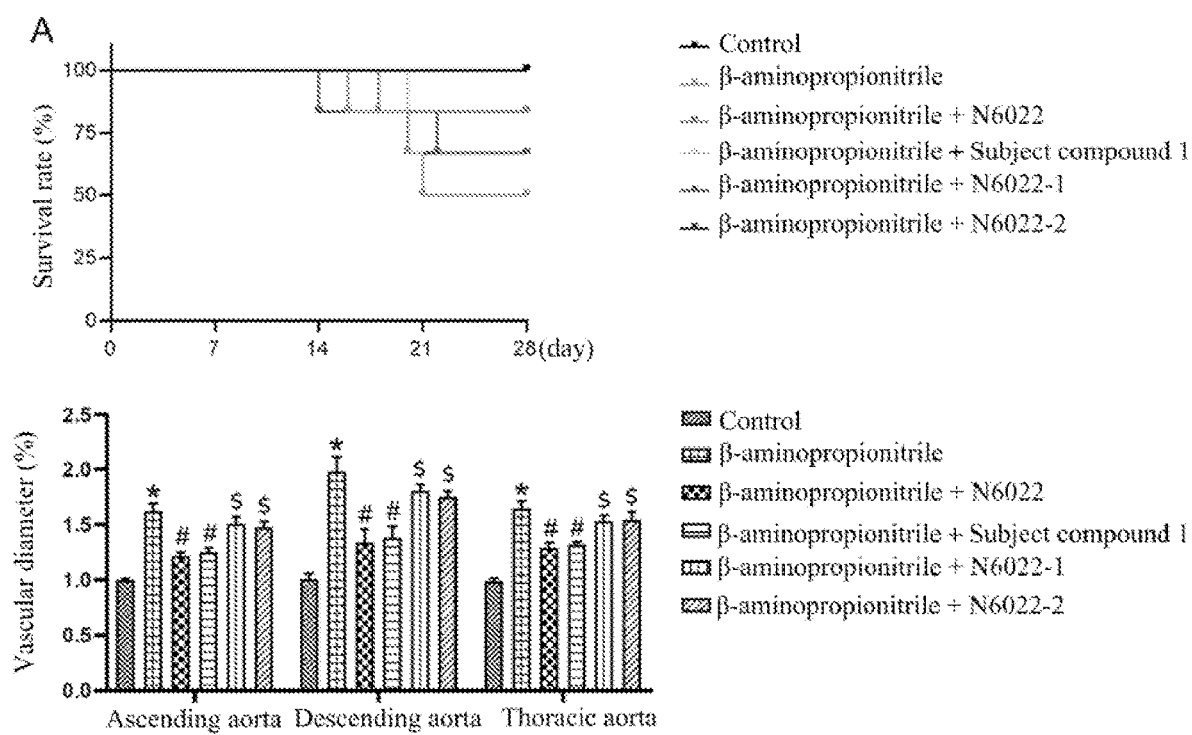
FIG. 7: Study of the oral efficacy of the subject compound 1 on aneurysm/dissection diseases.

FIG. 7 shows study of the oral efficacy of the subject compound 1 on aneurysm/dissection diseases. 3-week-old male C57BL/6J mice were given with β-aminopropionitrile-containing drinking water for 4 weeks to induce aortic aneurysm/dissection, and were intravenously injected with N6022 (1 mg/kg/day), gavaged with the subject compound 1 (6 mg/kg/day), gavaged with N6022-1 (5.6 mg/kg/day) and gavaged with N6022-2 (5.3 mg/kg/day) respectively every day, where A: the survival rate of the mice was detected; and B: the aortas of the mice were isolated, and the maximum diameter of the ascending aorta/descending aorta/thoracic aorta was quantified; and the pathologic expansion of the aortas was detected; *P<0.05 vs Control, #P<0.05 vs β-aminopropionitrile, $P<0.05 vs β-aminopropionitrile+Subject compound 1, n=5.

The results show that oral administration of the subject compound 1 has an equivalent effect to the group intravenously injected with N6022 and a significantly better effect than the groups orally administered with N6022-1 and N6022-2; and the experiments above indicate that oral administration of the subject compound 1 shows desirable therapeutic effect on aortic aneurysm/dissection diseases.

What is claimed is:
1. A thiazolone derivative of N6022 having a characteristic structure which is:

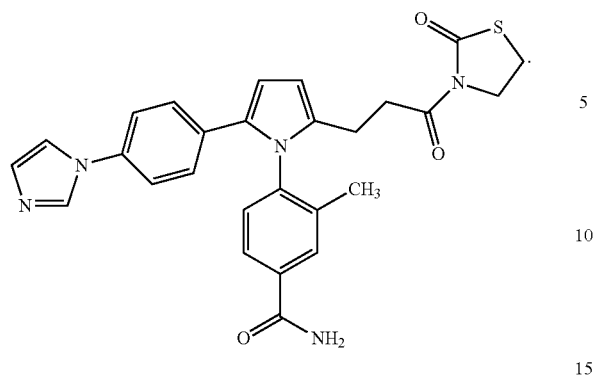

2. A method for treating of a disease in a subject comprising administration of a therapeutically effective amount of the thiazolone derivative of N6022 of claim 1 or a pharmaceutically acceptable salt thereof to the subject in need thereof, wherein the disease is selected from the group consisting of asthma, cystic fibrosis, diabetic vascular complications, aortic aneurysm/dissection.

* * * * *